US010980719B2

(12) United States Patent
Hinrichs et al.

(10) Patent No.: US 10,980,719 B2
(45) Date of Patent: Apr. 20, 2021

(54) ORAL CARE PRODUCT AND METHODS OF USE AND MANUFACTURE THEREOF

(71) Applicant: Colgate-Palmolive Company, New York, NY (US)

(72) Inventors: Ruth Hinrichs, Therwil (CH); Andre Brunella, Dornach (CH); Turan Matur, Binningen (CH)

(73) Assignee: Colgate-Palmolive Company, New York, NY (US)

( * ) Notice: Subject to any disclaimer, the term of this patent is extended or adjusted under 35 U.S.C. 154(b) by 16 days.

(21) Appl. No.: 16/067,647

(22) PCT Filed: Dec. 30, 2015

(86) PCT No.: PCT/US2015/068157
§ 371 (c)(1),
(2) Date: Jul. 2, 2018

(87) PCT Pub. No.: WO2017/116444
PCT Pub. Date: Jul. 6, 2017

(65) Prior Publication Data
US 2019/0000731 A1    Jan. 3, 2019

(51) Int. Cl.
| A61K 8/19 | (2006.01) |
| A61Q 11/00 | (2006.01) |
| A61K 8/34 | (2006.01) |
| A61K 8/37 | (2006.01) |
| A01N 59/16 | (2006.01) |
| A01N 31/02 | (2006.01) |
| A61K 8/21 | (2006.01) |

(52) U.S. Cl.
CPC ............... *A61K 8/19* (2013.01); *A01N 31/02* (2013.01); *A01N 59/16* (2013.01); *A61K 8/21* (2013.01); *A61K 8/34* (2013.01); *A61K 8/345* (2013.01); *A61K 8/37* (2013.01); *A61Q 11/00* (2013.01)

(58) Field of Classification Search
CPC ... A61K 8/19; A61K 8/21; A61K 8/37; A61K 8/345; A61Q 11/00
See application file for complete search history.

(56) References Cited

U.S. PATENT DOCUMENTS

| 4,828,822 A | 5/1989 | Muhlemann et al. |
| 9,855,200 B2 | 1/2018 | Campbell et al. |
| 9,937,115 B2 | 4/2018 | Haught et al. |
| 2010/0119461 A1 | 5/2010 | Bicard-Benhamou et al. |
| 2011/0028566 A1* | 2/2011 | McCaulley ............ A01N 31/04 514/729 |
| 2012/0082628 A1* | 4/2012 | Haught .................. A61Q 11/00 424/51 |
| 2013/0208375 A1 | 8/2013 | Argilagos et al. |
| 2013/0267570 A1 | 10/2013 | Premachandran et al. |

FOREIGN PATENT DOCUMENTS

| DE | 1020100007646 A1 | 1/2011 |
| EP | 2774481 | 9/2014 |
| JP | 2001-348308 | 12/2001 |
| JP | 2006-104144 | 4/2006 |
| WO | 2001-034109 | 5/2001 |
| WO | 2012/044728 | 4/2012 |
| WO | 2015/158635 | 10/2015 |

OTHER PUBLICATIONS

International Search Report and Written Opinion of the International Searching Authority in International Application No. PCT/US2015/068157, dated Mar. 11, 2016.
Exerkate et al., 2010, "Different Response to Amine Fluoride by *Streptococcus* mutans and Polymicrobial Biofilms in a Novel High-Throughput Active Attachment Model," Caries Research 44:372-379.
Drstraetmans, 2013, Product Brochure "Dermosoft® OMP" Product Information Brochure.
Gupta et al., 1979, "Study of the antimicrobial and preservative activities of 2-phenylethanol and its esters," Chemical Abstracts Service STN Database AN: 1979:5872285 Abstract.
International Search Report and Written Opinion of the International Searching Authority in International Application No. PCT/US2015/068160, dated Mar. 24, 2016.
Thiemann et al. 2014, "The formulators guide to safe cosmetic preservation", Nov. 2014 Personal Care 39 https://www.dr-straetmans.de/dl/media/filer_public/7a/ef/7aef7f01-c566-425c-9c7b-500334a96b2a/review_article_about_the_development_and_trends_in_preservative_legislation_and_safe_alternatives_for the_future_verstatil_dermosoft.pdf.
Varvaresou et al., 2009, "Review Article: Self-preserving cosmetics". International Journal of Cosmetic Science 31:163-175.
Woodruff, 2014, "Cosmetic preservation," https://creative-developments.co.uk/wp-content/uploads/2013/10/Cosmetic-Preservation-2014.pdf.

* cited by examiner

*Primary Examiner* — Lezah Roberts

(57) ABSTRACT

This invention relates to a dentifrice comprising (i) at least one source of ionic tin; and (ii) an antibacterial system comprising caprylyl glycol together with 3-phenyl-1-propanol, phenethyl salicylate, or both 3-phenyl-1-propanol and phenethyl salicylate, as well as to methods of using and of making these compositions.

13 Claims, No Drawings

ORAL CARE PRODUCT AND METHODS OF USE AND MANUFACTURE THEREOF

FIELD

This invention relates to oral care compositions, and in particular to dentifrice compositions comprising (i) at least one source of ionic tin; and (ii) an antibacterial system comprising caprylyl glycol and one or both of 3-phenyl-1-propanol and phenethyl salicylate, as well as to methods of using and of making these compositions.

BACKGROUND

Gingival inflammation is an early stage of gum disease that affects millions of people. If not treated, gingival inflammation can lead to periodontal disease, and tooth loss. Since bacteria are the main cause of gingival inflammation, antibacterial efficacy is recognized as a prerequisite for chemical treatment of irritated gums and protection against gingival inflammation.

Accordingly, there exists a need for improved antibacterial compositions effective against bacteria that cause gingival inflammation.

BRIEF SUMMARY

It has surprisingly been found that a combination of caprylyl glycol and one or both of 3-phenyl-1-propanol and phenethyl salicylate, can provide excellent antibacterial efficacy in a dentifrice containing tin ions. The compositions of the invention are galenically stable and show considerably improved antibacterial efficacy. Thus, in some embodiments, the present disclosure provides dentifrice compositions comprising at least one source of ionic tin; and an antibacterial system comprising caprylyl glycol; and one or both of 3-phenyl-1-propanol and phenethyl salicylate.

In some embodiments, the caprylyl glycol is present in an amount of from 0.01% to 1.2%; for example 0.2% to 1%; for example 0.4% to 0.8% by weight of the composition; the 3-phenyl-1-propanol, if present, is in an amount of from 0.01% to 0.2%; for example 0.02% to 0.1%; for example 0.04% to 0.08% by weight of the composition; and the phenethyl salicylate, if present, is in an amount of from 0.01% to 1.2%; for example 0.2% to 1%; for example 0.4% to 0.8% by weight of the composition.

In some embodiments, the source of ionic tin is a stannous ion source, or a stannic ion source, such as stannous fluoride, stannous chloride, stannic fluoride, stannic chloride, stannic acetate and stannous acetate or a combination thereof. Preferably, the source of ionic tin is a stannous ion source, for example stannous fluoride, stannous chloride, or stannous acetate, and more preferably stannous chloride.

In some embodiments, the present compositions further comprise a fluoride ion source which is not a tin salt, for example an organic fluoride, such as amine fluoride (i.e., N,N,N'-tris(2-hydroxyethyl)-N'-octadecyl-1,3-diaminopropane dihydrofluoride). In some further embodiments, the compositions further comprise at least one $C_3$ to $C_7$ α-hydroxy acid; or $C_4$ to $C_6$ α-hydroxy acid, or a salt thereof, which is preferably selected from malic acid, tartaric acid, α-hydroxy glutaric acid, gluconic acid, or a salt thereof, with sodium-D-gluconate being preferred.

In further embodiments, the dentifrice compositions of the disclosure further include at least one solvent, for example a propylene glycol. In further embodiments, the dentifrice compositions further include one or more abrasives selected from silica abrasives, calcium phosphate abrasives, calcium pyrophosphate, and calcium carbonate abrasives; for example high cleaning silica abrasives and small particle size silica abrasives.

In further embodiments, the dentifrice compositions of the present disclosure further include one or more thickening silicas. Thickening silicas are synthetic silicas comprising fumed silicas, amorphous precipitated silicas and gel silicas. The preferred thickening silicas include colloidal gel silicas, Aerosil™ 200 silica, available from Evonik Industries, Syloblanc™ silicas such as Syloblanc™ 34 silica, and Sylodent™ silicas such as Sylodent™ 614T, available from W.R. Grace.

In further embodiments, the dentifrice compositions further include one or more humectants, sweeteners, flavorings, sensates, fragrances, dyes, pigments and/or odor neutralizing agents. In further embodiments, the dentifrice compositions further include one or more foaming agents.

The present disclosure further provides methods for using and making the compositions.

The present disclosure further encompasses methods comprising applying an effective amount of a dentifrice as disclosed herein to the oral cavity, e.g., by brushing, to a subject in need thereof, to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity.

DETAILED DESCRIPTION

As used herein, an amount of a substance expressed as "%, by weight of the composition" is intended to mean the percentage by weight of that substance based on the total weight of the composition.

The present disclosure thus provides, in a first embodiment, oral care composition (Composition 1.0), comprising:
at least one source of ionic tin; and
an antibacterial system comprising:
caprylyl glycol; and
3-phenyl-1-propanol, or phenethyl salicylate, or a mixture thereof;
wherein the composition is a dentifrice; for example, any of the following compositions:
1.1. Composition 1.0, wherein:
the caprylyl glycol is present in an amount of from 0.01% to 1.2% by weight of the composition;
the 3-phenyl-1-propanol, if present, is in an amount of from 0.01% to 0.2% by weight of the composition; and
the phenethyl salicylate, if present, is in an amount of from 0.01% to 1.2% by weight of the composition.
1.2. Composition 1.0 or 1.1, wherein:
the caprylyl glycol is present in an amount of from 0.2% to 1% by weight of the composition;
the 3-phenyl-1-propanol, if present, is in an amount of from 0.02% to 0.1% by weight of the composition; and
the phenethyl salicylate, if present, is in an amount of from 0.2% to 1% by weight of the composition.

1.3. Composition 1.0 or 1.1, wherein:
the caprylyl glycol is present in an amount of from 0.4% to 0.8% by weight of the composition;
the 3-phenyl-1-propanol, if present, is in an amount of from 0.04% to 0.08% by weight of the composition; and
the phenethyl salicylate, if present, is in an amount of from 0.4% to 0.8% by weight of the composition.

1.4. Any of the foregoing compositions wherein the composition comprises at least one stannous ion source, at least one stannic ion source or a combination thereof.

1.5. Any of the foregoing compositions wherein the composition comprises at least one stannous ion source.

1.6. Any of the foregoing compositions wherein the at least one ionic tin source is selected from stannous fluoride, stannous chloride, stannic fluoride, stannic chloride, stannic acetate and stannous acetate.

1.7. Any of the foregoing compositions wherein the at least one ionic tin source comprises stannous chloride.

1.8. Any of the foregoing compositions wherein the tin ions are present in an amount of from 0.01% to 0.10% by weight of the composition.

1.9. Any of the foregoing compositions wherein the tin ions are present in an amount of from 0.1% to 0.6% by weight of the composition.

1.10. Any of the foregoing compositions wherein the tin ions are present in an amount of from 0.2% to 0.5% by weight of the composition.

1.11. Any of the foregoing compositions wherein the tin ions are present in an amount of from 0.3% to 0.4% by weight of the composition.

1.12. Any of the foregoing compositions further comprising a fluoride ion source which is not a tin salt.

1.13. Any of the foregoing compositions further comprising an organic fluoride.

1.14. Composition 1.13, wherein the organic fluoride is present in an amount sufficient to provide fluoride ions in an amount of from 0.05%-0.3% by weight of the composition; or from 0.1% to 0.2% by weight of the composition; or about 0.15% by weight of the composition.

1.15. Composition 1.14, wherein the organic fluoride is amine fluoride (i.e. N,N,N'-tris(2-hydroxyethyl)-N'-octadecyl-1,3-diaminopropane dihydrofluoride).

1.16. Any of the foregoing compositions further comprising amine base in an amount of from 0.1% to 2%; or from 0.5 to 1%, by weight of the composition.

1.17. Any of the foregoing compositions further comprising at least one chelating agent, for example a $C_3$ to $C_7$ α-hydroxy acid; or a $C_4$ to $C_6$ α-hydroxy acid, or salt thereof.

1.18. Composition 1.16, wherein the salt of the at least one α-hydroxy acid is sodium-D-gluconate.

1.19. Composition 1.17, wherein the sodium-D-gluconate is present in an amount of from 0.01% to 2%; or from 1% to 2%; or about 0.5%; or about 1.5%, by weight of the composition.

1.20. Any of the foregoing compositions further comprising one or more abrasives selected from silica abrasives, calcium phosphate abrasives, calcium pyrophosphate, and calcium carbonate abrasives.

1.21. Composition 1.20, wherein the one or more abrasives are selected from silica abrasives, for example high cleaning silica abrasives and small particle size silica abrasives.

1.22. Any of the foregoing compositions, further comprising one or more thickeners, for example thickening silicas.

1.23. Any of the foregoing compositions further comprising a foaming agent, for example a betaine, for example cocamidopropyl betaine.

1.24. Any of the foregoing compositions further comprising one or more humectants, binders, sweeteners, flavorings, sensates, fragrances, colorants, dyes, pigments and/or odor neutralizing agents.

1.25. Any of the foregoing compositions further comprising water in an amount of from 10% to 50% by weight of the dentifrice.

1.26. Any of the foregoing compositions wherein the antibacterial system comprises caprylyl glycol and 3-phenyl-1-propanol.

1.27. Any of the foregoing compositions wherein the antibacterial system comprises caprylyl glycol and phenethyl salicylate.

1.28. Any of the foregoing compositions effective upon application to the oral cavity, e.g., by brushing, to (i) reduce or inhibit gingivitis, (ii) promote healing of sores or cuts in the mouth, (iii) inhibit microbial biofilm formation in the oral cavity, (iv) treat, relieve or reduce dry mouth, (v) clean the teeth and oral cavity (vi) promote systemic health, including cardiovascular health, e.g., by reducing potential for systemic infection via the oral tissues.

1.29. A composition obtained or obtainable by combining the ingredients as set forth in any of the foregoing compositions.

In another embodiment, the disclosure provides a method (Method 1) to:
(i) reduce or inhibit formation of dental caries,
(ii) reduce, repair or inhibit pre-carious lesions of the enamel,
(iii) reduce or inhibit demineralization and promote remineralization of the teeth,
(iv) reduce hypersensitivity of the teeth,
(v) reduce or inhibit gingivitis,
(vi) promote healing of sores or cuts in the oral cavity,
(vii) reduce levels of acid producing bacteria,
(viii) reduce or inhibit microbial biofilm formation in the oral cavity,
(ix) reduce or inhibit plaque formation in the oral cavity,
(x) promote systemic health, or
(xi) clean teeth and oral cavity,
comprising applying an effective amount of a dentifrice composition according to any preceding composition to the oral cavity of a subject in need thereof.

In another embodiment, the present disclosure encompasses a method (Method 2) to improve oral health comprising applying an effective amount of a dentifrice according to any of the embodiments set forth above to the oral cavity of a subject in need thereof.

In a further embodiment, the present disclosure provides a method (Method 3) for preparing a dentifrice comprising: combining together (i) at least one source of ionic tin; (ii) caprylyl glycol; and either (iiia) 3-phenyl-1-propanol; or (iiib) phenethyl salicylate; or (iiic) both 3-phenyl-1-propanol and phenethyl salicylate, together with a source of fluoride ions, wherein the source of fluoride ions is separate from the source of ionic tin.

In a further embodiment, the present disclosure provides the use of any of the foregoing oral care dentifrice compositions to:

(i) reduce or inhibit formation of dental caries,
(ii) reduce, repair or inhibit pre-carious lesions of the enamel,
(iii) reduce or inhibit demineralization and promote remineralization of the teeth,
(iv) reduce hypersensitivity of the teeth,
(v) reduce or inhibit gingivitis,
(vi) promote healing of sores or cuts in the oral cavity,
(vii) reduce levels of acid producing bacteria,
(viii) reduce or inhibit microbial biofilm formation in the oral cavity,
(ix) reduce or inhibit plaque formation in the oral cavity,
(x) promote systemic health, or
(xi) clean teeth and oral cavity;
in a subject in need thereof.

The present disclosure further provides the use of the combination of a source of ionic tin, caprylyl glycol and one or both of 3-phenyl-1-propanol and phenethyl salicylate, in the manufacture of a composition of the invention, e.g., for use in any of the indications set forth in the above method.

The present disclosure further provides a method (Method 4) to increase the antibacterial efficacy of a dentifrice comprising formulating the dentifrice to comprise caprylyl glycol and 3-phenyl-1-propanol; or caprylyl glycol and phenethyl salicylate; or caprylyl glycol and both 3-phenyl-1-propanol and phenethyl salicylate; for example:

4.1. Method 4, wherein:
the caprylyl glycol is present in an amount of from 0.01% to 1.2% by weight of the composition;
the 3-phenyl-1-propanol, if present, is in an amount of from 0.01% to 0.2% by weight of the composition; and
the phenethyl salicylate, if present, is in an amount of from 0.01% to 1.2% by weight of the composition;

4.2. Method 4.0 or 4.1, wherein the dentifrice further comprises a source of tin ions in an amount of from 0.1% to 0.6% by weight of the dentifrice;

4.3. Method 4.0, 4.1 or 4.2, wherein the dentifrice further comprises amine fluoride in an amount of from 1% to 3% by weight of the composition.

In some embodiments, the compositions of the present disclosure are intended to be used as a dentifrice, delivering a dose of the ionic tin, fluoride and antibacterial system comprising caprylyl glycol and one or both of 3-phenyl-1-propanol and phenethyl salicylate, as well as other added actives, to the oral cavity of a subject.

The compositions of the present disclosure are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Source of Ionic Tin

The dentifrice compositions of the present disclosure comprise a source of ionic tin. In certain embodiments the source of ionic tin is a source of stannous (Sn(II)) or stannic (Sn(IV)) ions. In certain embodiments the source of ionic tin comprises at least one stannous ion source, at least one stannic ion source or a combination thereof. In certain embodiments the source of ionic tin comprises at least one stannous ion source. In certain embodiments the source of ionic tin comprises a stannous salt. In certain embodiments the source of ionic tin is selected from water-soluble tin salts such as stannous fluoride, stannous chloride, stannic fluoride, stannic chloride, stannic acetate, stannous acetate and combinations thereof. In certain embodiments the source of ionic tin is selected from stannous fluoride, stannous chloride, stannous acetate and combinations thereof. In certain embodiments the source of ionic tin comprises stannous fluoride, stannous chloride and/or combinations thereof. In certain preferred embodiments, the source of ionic tin is a stannous ion source. In particularly preferred embodiments the source of ionic tin is stannous chloride. In certain embodiments separate soluble stannous and chloride salts may be used to provide stannous chloride in situ. Alternatively, stannous chloride salt may be added to the composition directly.

In certain embodiments the ionic tin is present in the dentifrice composition in an amount (assuming complete dissolution of the tin salt) sufficient to provide tin ions, preferably stannous ions, in an amount of from 0.01% to 1% by weight of the oral care dentifrice composition; or in an amount of from 0.1% to 0.6% by weight of the oral care dentifrice composition; or in an amount of from 0.2% to 0.5% by weight of the oral care dentifrice composition; or in an amount of from 0.3% to 0.4% by weight of the oral care dentifrice composition. In some embodiments, the source of ionic tin is stannous chloride, in an amount of from 0.1% to 1% by weight, for example from 0.2% to 0.9% by weight; for example from 0.3% to 0.7 by weight, for example 0.4% to 0.7% by weight, for example from 0.5% to 0.6% by weight.

Antibacterial System

The compositions disclosed herein include an antibacterial system that comprises caprylyl glycol (octane-1,2-diol; CAS Registry Number 1117-86-8) and one or both of 3-phenyl-1-propanol (3-phenylpropan-1-ol; CAS Registry Number 122-97-4) and phenethyl salicylate (2-Phenylethyl salicylate; CAS Registry Number 87-22-9).

In some embodiments, the caprylyl glycol is present in an amount of from 0.01% to 1.2%; for example 0.2% to 1%; for example 0.4% to 0.8% by weight of the composition; the 3-phenyl-1-propanol, if present, is in an amount of from 0.01% to 0.2%; for example 0.02% to 0.1%; for example 0.04% to 0.08% by weight of the composition; and the phenethyl salicylate, if present, is in an amount of from 0.01% to 1.2%; for example 0.2% to 1%; for example 0.4% to 0.8% by weight of the composition.

It has been discovered that this combination provides superior antibacterial properties in oral care dentifrice compositions, and in particular, those in accordance with the present disclosure that contain a source of ionic tin.

In some embodiments, the caprylyl glycol and 3-phenyl-1-propanol can be present in the dentifrice compositions in a ratio of from 15:1 to 5:1; for example from 12:1 to 8:1; for example about 10:1, respectively.

In some embodiments, the caprylyl glycol and phenethyl salicylate can be present in the dentifrice compositions in a ratio of from 5:1 to 1:5; for example from 2:1 to 2:2; for example about 1:1, respectively.

Fluoride Ion Source:

The dentifrice compositions may further include one or more fluoride ion sources, e.g., soluble fluoride salt that is not a tin salt. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference.

Representative non-tin fluoride ion sources include, but are not limited to, sodium fluoride, potassium fluoride, sodium monofluorophosphate, sodium fluorosilicate, ammonium fluorosilicate, amine fluoride, ammonium fluoride, and combinations thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride. In certain embodiments the non-tin fluoride ion source includes or consists of an organic fluoride, also known as organic amine fluorides. Representative examples of organic fluorides can be found in, for example, European Patent No. EP19970911101, incorporated by reference herein in its entirety. One preferred organic fluoride is referred to herein as "amine fluoride", (or "AmF"), and is the compound N,N,N'-tris(2-hydroxyethyl)-N'-octadecyl-1,3-diaminopropane dihydrofluoride (also known as "Olaflur", and sometimes written as N,N,N'-tris(2-hydroxyethyl)-N'-octadecyl propane-1,3-diamine dihydrofluoride). While the term "amine fluoride" as used herein denotes the compound N,N,N'-tris(2-hydroxyethyl)-N'-octadecyl-1,3-diaminopropane dihydrofluoride, it will be appreciated that any of the variety of organic fluorides that are known to be useful in mouth rise compositions can be employed instead of, or in addition to, amine fluoride. In certain embodiments, the organic fluoride is present in an amount sufficient to provide fluoride ions in an amount of from 0.05%-0.3% by weight of the composition; or from 0.1% to 0.2% by weight of the composition; or about 0.15% by weight of the composition. In certain embodiments, the organic fluoride is amine fluoride, in an amount of from 0.05% to 3% by weight; or from 1% to 3% by weight, or 1.5% to 2.4% by weight, or from 1.7% to 2.1% by weight, or about 1.9%, by weight of the composition. In certain embodiments, the compositions of the invention include amine fluoride and stannous chloride in a weight ratio of from 6:1 to 1:1; from 5:1 to 2:1; or from 4:1 to 3:1; or about 3.5:1.

In certain embodiments, the stannous chloride and amine fluoride together comprise from 1 to 4%; or from 2% to 3%; or about 2.5% by weight of the composition.

As used herein, the term "amine base" is intended to denote the base portion of amine fluoride—i.e., the compound N,N,N'-tris(2-hydroxyethyl)-N'-octadecyl-1,3-diaminopropane. In some embodiments, the present compositions contain an amount of amine base in addition to the amine fluoride. In some embodiments, the compositions include amine base in an amount of from 0.1% to 2%; or from 0.5 to 1%, by weight of the composition.

α-Hydroxy Acid

In some embodiments, the compositions of the present disclosure include at least one α-hydroxy acid or salt thereof. In some embodiments, the salt of the at least one α-hydroxy acid is the sodium salt or the potassium salt. In some embodiments, the salt is the sodium salt. In some embodiments, the at least one α-hydroxy acid is a $C_3$ to $C_7$ α-hydroxy acid, or a $C_4$ to $C_6$ α-hydroxy acid. In certain embodiments, the at least one α-hydroxy acid is malic acid, tartaric acid, α-hydroxy glutaric acid, gluconic acid, or a salt thereof. In certain embodiments, the at least one α-hydroxy acid or salt thereof is sodium-D-gluconate. In some embodiments, the sodium-D-gluconate is present in an amount of from 0.01% to 2%; for example from 1% to 2%; for example about 1.5%, by weight of the composition.

Surfactant

In some embodiments, the compositions of the present disclosure include at least one surfactant or solubilizer. Suitable surfactants include neutral surfactants (such as polyoxyethylene hydrogenated castor oil or fatty acids of sugars), anionic surfactants (such as sodium lauryl sulfate), cationic surfactants (such as the ammonium cation surfactants) or zwitterionic surfactants. These surfactants or solubilizers may be present in amounts of typically 0.01% to 2%; or from 1% to 2%; or about 1.5%, by weight of the composition. In some preferred embodiments, the at least one surfactant is polyethylene glycol or propylene glycol, with propylene glycol being preferred.

Abrasives

The compositions of the present disclosure, e.g. Compositions 1-1.29, preferably include abrasives. In some embodiments, the compositions include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof. In some embodiments, the compositions comprise a high cleaning silica and a small particle size silica.

Suitable high cleaning silicas may be e.g., a silica as described in United States Patent Application 2012/0100193 (the contents of which are incorporated herein by reference), e.g., Sylodent VP5 from W.R.Grace. Suitable small particle size silicas include high RDA high abrasive silicas, for example Sorbosil AC33 from PQ Corporation.

Other silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention.

Foaming Agents

The oral care compositions of the present disclosure also may include an agent to increase the amount of foam that is produced when the oral cavity is brushed. Illustrative examples of agents that increase the amount of foam include, but are not limited to polyoxyethylene and certain polymers including, but not limited to, alginate polymers. Where present, the amount of foaming agent in the oral care composition is preferably about 0.01 to about 3% by weight, about 1% to about 3% by weight, for example about 2% by weight. In some embodiments, the foaming agent is a betaine, for example cocamidopropyl betaine.

Polyhydric Alcohol

In any of the above embodiments, the compositions may further comprise one or more polyhydric alcohols such as xylitol, glycerine, sorbitol, propylene glycol and combinations thereof. In certain embodiments the compositions may optionally comprise from about 0.10% to about 60% polyhydric alcohol by weight of the composition. In certain embodiments the compositions may comprise glycerin in an amount of from 20% to 60%, for example from 30% to 50%, for example from 40% to 45%, by weight of the composition. The polyhydric alcohols can also serve as humectants, as discussed below.

Sweeteners

In any of the above embodiments, the compositions may further comprise a sweetener such as, for example, saccharin, for example sodium saccharin, acesulfam, neotame, cyclamate or sucralose; natural high-intensity sweeteners such as thaumatin, stevioside or glycyrrhizin; or such as sorbitol, xylitol, maltitol or mannitol. One or more such sweeteners may be present in an amount of from 0.005% to 5% by weight, for example 0.01% to 1%, for example 0.01% to 0.5%, by weight of the composition.

Colorants

One or more colorants can be included in the compositions of the present disclosure. Colorants may include pigments, dyes, lakes and agents imparting a particular color or visual quality to the composition. Any orally acceptable colorant can be used. One or more colorants may optionally be present in the compositions in an amount of from 0.001% to 2%, for example from 0.001% to 0.01%, for example from 0.001% to 0.005% of the composition by weight.

Humectants

Humectants can reduce evaporation and also contribute towards preservation by lowering water activity, and can also impart desirable sweetness or flavor to compositions. Suitable humectants include edible polyhydric alcohols such as glycerin, sorbitol, xylitol, propylene glycol as well as other polyols and mixtures of these humectants.

Other useful materials may also include orally acceptable alcohols, or polymers, e.g., such as polyvinylmethyl ether maleic acid copolymers, polysaccharides (e.g. cellulose derivatives, for example carboxymethyl cellulose, or polysaccharide gums, for example xanthan gum or carrageenan gum). In some embodiments, the humectant can be present in an amount of from 20% to 60%, for example from 30% to 50%, for example from 40% to 45%, by weight of the composition. In some embodiments, the present compositions may include at least one humectant that can be, for example, glycerin.

Preservatives

A wide variety of preservatives can be used in the compositions of the present disclosure. Suitable preservatives include, for example, sodium benzoate, potassium sorbate, methylisothiazolinone, paraben preservatives, for example methyl p-hydroxybenzoate, propyl p-hydroxybenzoate, and mixtures thereof.

Flavoring Agents

The oral care compositions of the present disclosure may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. The flavoring agent is typically incorporated in the oral composition at a concentration of 0.01 to 3% by weight.

Anti-Calculus Agents

In some embodiments, the oral compositions of the present disclosure comprise antitartar agents to prevent and/or minimize calculus formation. One or more of such agents can be present. Suitable anticalculus agents include without limitation: stannous, copper, magnesium and strontium salts, dimethicone copolyols such as cetyl dimethicone copolyol, glucoamylase, glucose oxidase, urea, calcium lactate, calcium glycerophosphate, strontium polyacrylates and chelating agents such as citric and tartaric acids and alkali metal salts thereof, and salts of EDTA, for example tetrasodium EDTA; and phosphates and polyphosphates. Phosphate and polyphosphate salts are generally employed in the form of their wholly or partially neutralized water soluble cationic species (e.g., potassium, sodium or ammonium salts, and any mixtures thereof). Thus, useful inorganic phosphate and polyphosphate salts illustratively include monovalent cations with monobasic, dibasic and tribasic phosphates; tripolyphosphate and tetrapolyphosphate; mono-, di-, tri- and tetra-pyrophosphates; and cyclophosphates (also generally known in the art as "metaphosphates"). Useful monovalent cations of such phosphate salts include hydrogen, monovalent metals including alkali metals, and ammonium, for example.

Sensates

In some embodiments, the oral compositions of the present disclosure comprise one or more sensates—i.e., ingredients which impart some kind of sensation to the oral cavity. Suitable sensates include without limitation, physiological cooling agents including 1-menthol and 3-(1-menthoxy)propane-1,2-diol, peppermint oil, N-substituted-p-menthane-3-carboxamides, acyclic tertiary and secondary carboxamides, and 3-1-menthoxy propan-1,2-diol (see, e.g., PCT Published Application Number WO 97/06695); heating and/or warming sensates such as, for example and not imitated to, vanillyl alcohol n-butyl ether (vanillyl butyl ether), vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, iso-propyl alcohol, iso-amyl alcohol, benzyl alcohol, chloroform, eugenol, cinnamon oil, connamic aldehyde and phosphate derivatives of same; materials that are known to cause a tingling, numbing and/or stinging sensation and are used in foods as popular spice and/or herb condiments; and combinations thereof.

Odor Neutralizing Agents

In some embodiments, the oral compositions of the present disclosure comprise one or more odor-neutralizing agents. Suitable odor neutralizing agents include, without limitation, chlorine dioxide; peroxides such a hydrogen peroxide; chlorite salts and bicarbonate salts,—e.g. sodium chlorite and sodium bicarbonate; essential oils such as eucalyptol, menthol, methyl salicylate and thymol; flavor cocktails; and zinc salts such as, for example and not limited to, zinc chloride, zinc citrate, zinc acetate, zinc sulfate, and zinc phenolsulfate.

The compositions of the present disclosure may comprise a saliva stimulating agent useful, for example, in amelioration of dry mouth. One or more saliva stimulating agents are optionally present in saliva stimulating effective total amount.

The compositions of the present disclosure may include antisensitivity agents. Such agents may be added in effective amounts, e.g., from about 0.1 wt. % to about 5 wt. % by weight based on the total weight of the composition, depending on the agent chosen.

In any of the above embodiments, the compositions may further comprise a pH adjuster. For example the compositions may comprise an acid or base in an amount sufficient to adjust the pH of the compositions such that the compositions have a pH of from 4.0 to 8.0.

Water

Water is present in the oral compositions of the present disclosure. Water, employed in the preparation of commercial oral compositions should be deionized and free of organic impurities. Water commonly makes up the balance of the compositions and includes 10% to 50%, e.g., 20% to 40%, by weight of the oral compositions. This amount of water includes the free water which is added plus that amount which is introduced with other materials or any components of the compositions described herein.

As will be evident to one of skill in the art, some components of the present compositions may perform multiple functions, and the identification of a compound as having one function herein is not meant to exclude its use for other functions in a particular composition. For example, a compound such as xylitol may function in the compositions of the invention as a sweetener, but also act as a humectant, and a compound such as propylene glycol can act as both a solvent and a humectant.

The present invention in its method aspect involves applying to the oral cavity a safe and effective amount of the compositions described herein. The compositions and methods according to the present disclosure are useful, inter alia, to clean the teeth in the oral cavity of a mammal, for example a human, and provide improved methods of promoting oral health and/or systemic health, including cardiovascular health, e.g., by reducing bacterial levels in the oral cavity.

Enhancing oral health also provides benefits in systemic health, as the oral tissues can be gateways for systemic infections. Good oral health is associated with systemic health, including cardiovascular health. The compositions and methods of the invention are thus useful to enhance systemic health, including cardiovascular health.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

EXAMPLES

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1—Representative Formulation of the Invention

Tables 1 and 2 below show two representative formulations according to the invention, and two specific embodiments (Compositions 1 and 2).

TABLE 1

| Ingredient | Weight % Range | Weight % Range |
| --- | --- | --- |
| DI Water | 25-35 | 25-35 |
| Stannous Chloride | 0.1-1 | 0.1-1 |
| Amine Fluoride | 0.05-3 | 0.05-3 |
| Amine base | 0.1-2 | 0.1-2 |
| caprylyl glycol | 0.01-1.2 | 0.01-1.2 |
| 3-phenyl-1-propanol | 0.01-0.2 | 0 |
| Phenethyl salicylate | 0 | 0.01-1.2 |
| Glycerin | 20-60 | 20-60 |
| Hydrated silica | 5-30 | 5-30 |
| HEC (e.g., Tylose) | 0.5-5 | 0.5-5 |
| Sodium-D-gluconate | 0.01-2 | 0.01-2 |
| Cocamidopropyl betaine | 0.5-5 | 0.5-5 |
| Propylene glycol | 0.01-3 | 0.01-3 |
| Sweetener | 0.05-0.1 | 0.05-0.1 |
| Flavor | 0.5-5 | 0.5-5 |
| Color | 0.001-0.005 | 0.001-0.005 |

TABLE 2

| Ingredient | Composition 1 | Composition 2 |
| --- | --- | --- |
| DI Water, sweetener, flavor, color | 31.72 | 31.18 |
| Stannous Chloride | 0.57 | 0.57 |
| Amine Fluoride | 1.84 | 1.84 |
| Amine base | 0.72 | 0.72 |
| caprylyl glycol | 0.6 | 0.6 |
| 3-phenyl-1-propanol | 0.06 | 0 |
| Phenethyl salicylate | 0 | 0.6 |
| Glycerin | 42 | 42 |
| Hydrated silica | 15.5 | 15.5 |
| HEC (e.g., Tylose) | 2 | 2 |
| Sodium-D-gluconate | 1.55 | 1.55 |
| Cocamidopropyl betaine | 2 | 2 |
| Propylene glycol | 1.44 | 1.44 |

Galenically stable compositions (Compositions 1 and 2) were prepared as described above in Table 2.

A selected combination of efficacy parameters was assessed in different biofilm model tests, using the active-attachment biofilm model of Exterkate et al., Caries Research 2010; 44:372.379.

Experimental Specifications

Parameters: Viable counts (Log CFU/ml), lactate production (μM)

Treatment time: 10 min

Treatment schedule: 7 times; at 24 h, 32 h, 48 h, 56 h 72 h, 80 h and 96 h

Inoculum: Native saliva

Biofilm Formation: The biofilm model consists of a metal lid with 24 clamps carrying hydroxyapatite (HAP) disks. The model was inoculated in 24-well plates with native saliva. Biofilms were formed via active recruitment of bacteria onto free-hanging HAP disks. After an initial attachment phase of 8 hours under anaerobic conditions at 37° C., the biofilms were transferred into fresh growth media for maturation. Two lids were used for this assay.

Treatment: Treatment was performed after formation of a 24 hour biofilm. To begin with, the lid was moved up and down 10 times in growth medium to remove loose cells. The lid was then transferred to a 24-well plate containing 1.6 ml of dentifrice slurry (1 part dentifrice and two parts water (w/w)) and was incubated for 10 minutes at room temperature. The lid was subsequently transferred to a new plate for washing with 1.7 ml Cysteine Peptone Water (CPW) and moved up and down 10 times to wash away the treatment solutions. This procedure was performed three times, each time with fresh CPW in a 24-well plate. The biofilms were then transferred into growth media and incubated anaerobically at 37° C. up to the next treatment exposure. There were 4 biofilm replicates for each test product (N=4).

The following efficacy parameters were assessed in the biofilm model:

A) Colony Forming Unit (CFU) determination: Colony Forming Unit (CFU) determination was done by plating serial dilutions of the harvested biofilms at the end of the experiment. HAP disks were removed from the lid and transferred to 1.5 ml CPW for sonication. The sonication was carried out for 2 minutes with 30 pulses. The volume of each suspension was brought to 2 ml. The suspension was serially diluted, plated on TSA-blood agar plates and incubated anaerobically for 48-72 hours. CFUs were determined by colony counting. The fewer CFU (i.e., bacteria still able to reproduce) were recorded, the better the antimicrobial efficacy of the test product was.

B) Bacterial Viability I Metabolic Activity ATP Assay: The bacterial viability I metabolic activity ATP assay is a quick method to assess the viability of the bacteria in the biofilm after exposure to test products. The test quantitates the bacteria's ability to metabolize ATP which is a key indicator for integrity of bacterial cells. Lower fluorescence intensity translates into reduced bacterial viability.

C) Resazurin assay: The Resazurin assay determines the total biofilm metabolic activity. A low fluorescence intensity translates into reduced bacterial viability. See Pesch, K. L.; Simmert, U. (1929). "Combined assays for lactose and galactose by enzymatic reactions". Milchw. Forsch 8: 551, incorporated by reference in its entirety.

D) Live/dead staining: A low live/dead ratio indicates increased efficacy of test product.

E) Lactic Acid Formation: Lactic acid production was determined to assess the residual metabolic activity of biofilms after repeated exposure to test products. After the last treatment, the lid was placed on a plate containing Buffered Peptone Water+0.2% glucose. The plate was incubated anaerobically at 37° C. for 3 hours for lactic acid formation. Subsequently, the Buffered Peptone Water solution was transferred into eppendorf tubes and placed on a hot plate at 80° C. for 5 min to stop lactic acid production. After cooling to room temperature, the tubes were stored at −20° C. until analysis. Right before the assay, the tubes were centrifuged at 14,000 rpm for 10 minutes at 4° C. The assay was conducted using a L-Lactate Assay Kit according to the manufacturer's protocol (Cayman Chemical Company, Cat. No. 700510). The less lactic acid is formed in the test, the more impacted the oral microbiota was by the test product treatment. This test measures impact of test products on the share of bacteria contained in the mixed biofilm that are lactic acid formers.

Statistical Analysis: Statistical analysis was performed using Minitab 16 Software. ANOVA and Tukey test were performed on available CFU counts and lactic acid values. Statistically significant differences are displayed with letters. Products sharing a letter do not differ.

Example 2—Anti-Bacterial Efficacy of Stannous-Based Dentifrices

Compositions 1 and 2 were evaluated in different biofilm model tests described above against water (as a negative control), a commercial dentifrice containing $SnF_2$, AmF, and amine base (as a positive control), and a composition (Composition 3) containing the components of Compositions 1 and 2 other than AmF, Amine base, $SnCl_2$, caprylyl glycol, 3-phenyl-1-propanol and phenethyl salicylate. The dentifrice compositions are shown below in Table 3:

TABLE 3

| Composition | AmF (%) | Amine Base (%) | $SnCl_2$ (%) | $SnF_2$ (%) | Caprylyl Glycol (%) | 3-phenyl-1-propanol (%) | Phenethyl salicylate (%) |
|---|---|---|---|---|---|---|---|
| 1 | 1.84 | 0.72 | 0.57 | 0 | 0.6 | 0.06 | 0 |
| 2 | 1.84 | 0.72 | 0.57 | 0 | 0.6 | 0 | 0.6 |
| 3* | 0 | 0 | 0 | 0 | 0 | 0 | 0 |
| Commercial Dentifrice | 0.46 | 0.95 | 0 | 0.44 | 0 | 0 | 0 |
| Water | 0 | 0 | 0 | 0 | 0 | 0 | 0 |

*this formulation contains the other ingredients of compositions 1-2.

Compositions 1 and 2 showed either a similar or better activity or efficacy as compared with the commercial dentifrice in each of the tests performed (Bacterial Viability I Metabolic Activity ATP Assay; Resazurin assay; Lactic Acid Formation; Live/Dead staining and CFU determination). The results of the CFU determination for Compositions 1 and 2, and the commercial dentifrice, showed that only Composition 1 was statistically significantly different from the commercial dentifrice in its ability to impact biofilm grown for 24 hours prior to treatment. Nevertheless, both Compositions 1 and 2 were significantly different to water in both the 24 hour and 48 hour biofilm test.

In a separate experiment, a dentifrice containing 1.84% AmF/0.57% $SnCl_2$/and 0.72% amine base was used to evaluate the effect of similar compositions also containing caprylyl glycol plus 3-phenyl-1-propanol or caprylyl glycol plus phenethyl salicylate in the different biofilm model tests described above, as shown below in Table 4:

TABLE 4

| Composition | AmF (%) | Amine Base (%) | $SnCl_2$ (%) | SnF2 (%) | Caprylyl Glycol (%) | 3-phenyl-1-propanol (%) | Phenethyl salicylate (%) |
|---|---|---|---|---|---|---|---|
| 4 | 1.84 | 0.72 | 0.57 | 0 | 0 | 0 | 0 |
| 5 | 1.84 | 0.72 | 0.57 | 0 | 0.6 | 0.06 | 0 |
| 6 | 1.84 | 0.72 | 0.57 | 0 | 0.6 | 0 | 0.5 |
| Commercial Dentifrice (positive control) | 0.46 | 0.95 | 0 | 0.44 | 0 | 0 | 0 |
| Water (negative control | 0 | 0 | 0 | 0 | 0 | 0 | 0 |

Compositions 1 and 2 showed either a similar or better activity or efficacy as compared with the commercial dentifrice in each of the tests performed (Bacterial Viability I Metabolic Activity ATP Assay; Resazurin assay; CFU determination and Lactic Acid Formation).

The results show that the combination of caprylyl glycol and 3-phenyl-1-propanol; and the combination of caprylyl glycol and phenethyl salicylate are both very potent when combined with stannous ions. While not wishing to be bound by any particular theory, it is believed that the combination of 3-phenyl-1-propanol and caprylyl glycol; or caprylyl glycol and phenethyl salicylate, may increase the bioavailability of stannous ions and therefore indirectly improves the anti-bacterial profile, or, alternatively, may increase penetration of stannous ions into bacterial cells.

Example 3—Appearances of Compositions Over Time

The appearance (color and texture) of Compositions 1 and 2 were determined after 3 months at 40° C., and was found to be comparable to the commercial formulation. The commercial formulation was pale blue in color, and smooth, slightly liquescent, with no separation, whereas both Compositions 1 and 2 were blue in color, and standing toothpastes, that slipped from tube laminate, with no separation.

These results demonstrate that compositions of the present disclosure have acceptable stability.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight, in relation to the total weight of the composition. The amounts given are based on the active weight of the material.

Each of the patents, patent applications and other printed publications referred to herein are incorporated by reference in their entireties for all purposes.

What is claimed is:

1. A dentifrice comprising:
   at least one source of ionic tin; and
   an antibacterial system comprising:
      caprylyl glycol in an amount from 0.4% to 0.8% by weight of the composition; and
      3-phenyl-1-propanol in an amount from 0.04% to 0.08% by weight of the composition, or phenethyl salicylate in an amount of from 0.4% to 0.8% by weight of the composition, or a mixture thereof.

2. The dentifrice of claim 1 wherein the at least one ionic tin source is selected from the group consisting of stannous fluoride, stannous chloride, stannic fluoride, stannic chloride, stannic acetate and stannous acetate.

3. The dentifrice of claim 1 wherein the at least one ionic tin source comprises stannous chloride.

4. The dentifrice of claim 1 wherein the tin ions are present in an amount of from 0.01% to 1%, or from 0.1% to 0.6%, or from 0.2% to 0.5%, or from 0.3% to 0.4% by weight of the dentifrice.

5. The dentifrice of claim 1 further comprising an amine fluoride in an amount sufficient to provide fluoride ions in an amount of from 0.05% 0.3% by weight of the composition; or from 0.1% to 0.2% by weight of the composition; or about 0.15% by weight of the composition.

6. The dentifrice according to claim 1, further comprising at least one chelating agent $C_3$ to $C_7$ α-hydroxy acid; or a $C_4$ to $C_6$ α-hydroxy acid, or salt thereof; in an amount of from 0.01% to 2%; or from 1% to 2%; or about 1.5%, by weight of the composition.

7. The dentifrice according to claim 1, further comprising at least one surfactant in an amount of from 0.01% to 3%; or 1% to 2%; or about 1.5% by weight of the composition.

8. The dentifrice according to claim 1, further comprising one or more abrasives selected from silica abrasives, calcium phosphate abrasives, calcium pyrophosphate, and calcium carbonate abrasives.

9. The dentifrice according to claim 1, further comprising one or more thickening silicas; and further comprising a foaming agent.

10. The dentifrice of claim 1 further comprising water in an amount of from 10% to 50% by weight of the dentifrice.

11. The dentifrice of claim 1 wherein the antibacterial system comprises caprylyl glycol and 3-phenyl-1-propanol.

12. The dentifrice of claim 1 wherein the antibacterial system comprises caprylyl glycol and phenethyl salicylate.

13. A method to:
(i) reduce or inhibit formation of dental caries,
(ii) reduce, repair or inhibit pre-carious lesions of the enamel,
(iii) reduce or inhibit demineralization and promote remineralization of the teeth,
(iv) reduce hypersensitivity of the teeth,
(v) reduce or inhibit gingivitis,
(vi) promote healing of sores or cuts in the oral cavity,
(vii) reduce levels of acid producing bacteria,
(viii) reduce or inhibit microbial biofilm formation in the oral cavity,
(ix) reduce or inhibit plaque formation in the oral cavity,
(x) promote systemic health, or
(xi) clean teeth and oral cavity,
comprising applying an effective amount of a dentifrice according to claim 1 to the oral cavity of a subject in need thereof.

\* \* \* \* \*

UNITED STATES PATENT AND TRADEMARK OFFICE
CERTIFICATE OF CORRECTION

| | | |
|---|---|---|
| PATENT NO. | : 10,980,719 B2 | Page 1 of 1 |
| APPLICATION NO. | : 16/067647 | |
| DATED | : April 20, 2021 | |
| INVENTOR(S) | : Ruth Hinrichs et al. | |

It is certified that error appears in the above-identified patent and that said Letters Patent is hereby corrected as shown below:

On the Title Page

Under "FOREIGN PATENT DOCUMENTS", Line 1, delete "1020100007646" and insert -- 102010000746 --, therefor.

In the Claims

In Column 16, Line 46, in Claim 5, delete "0.05% 0.3%" and insert -- 0.05% - 0.3% --, therefor.

Signed and Sealed this
Third Day of September, 2024

Katherine Kelly Vidal
*Director of the United States Patent and Trademark Office*